United States Patent [19]

Lesage

[11] Patent Number: 5,362,495
[45] Date of Patent: Nov. 8, 1994

[54] INSERT MATERIAL FOR WIDENING THE GINGIVAL SULCUS

[76] Inventor: Patrick Lesage, 9, rue Constantine, 35400 Saint-Malo, France

[21] Appl. No.: 778,229
[22] PCT Filed: Jun. 13, 1989
[86] PCT No.: PCT/FR90/00417
 § 371 Date: Dec. 10, 1991
 § 102(e) Date: Dec. 10, 1991
[87] PCT Pub. No.: WO90/15587
 PCT Pub. Date: Dec. 27, 1990

[30] Foreign Application Priority Data

Jun. 13, 1989 [FR] France ................... 89 07812

[51] Int. Cl.$^5$ ............ A61K 9/14; A61K 47/36; A61C 5/02
[52] U.S. Cl. .................... 424/435; 424/434; 433/224; 433/228.1; 433/229; 514/782
[58] Field of Search ............ 424/434, 435, 485; 433/224, 228.1, 229; 514/777, 782

[56] References Cited

U.S. PATENT DOCUMENTS 4,650,665 3/1987 Kronenthal et al. ............... 424/435

FOREIGN PATENT DOCUMENTS 0092329 10/1983 European Pat. Off. .
3736155 5/1989 Germany .
3737552 5/1989 Germany .

Primary Examiner—Thurman K. Page
Assistant Examiner—C. Azpuru
Attorney, Agent, or Firm—Armstrong, Westerman Hattori, McLeland & Naughton

[57] ABSTRACT

The present invention has for its object an insert material used for widening the gingival sulcus, substantially without bleeding or oozing, particularly in order to make a cast for a dental prosthesis.

According to the invention, this material takes the form of a biocompatible paste which is injectable for external use and preferably hydrophilic, whose viscosity is of between about 13000 and about 30000 Pascals.second.

Application: dental surgery.

21 Claims, 2 Drawing Sheets

INSERT MATERIAL FOR WIDENING THE GINGIVAL SULCUS

The present invention has for its object an insert material useful for widening the gingival sulcus, substantially without bleeding or oozing.

It is known that the gingival sulcus is a virtual space, located between the tooth and the gum, which it is necessary to widen for example prior to making an impression or for effecting various treatments, such as for example bondings, seals or the treatment of caries in sub-gingival zone, in order to obtain a clean, dry operative field.

The presently known techniques for widening the gingival sulcus may be divided into two groups depending on whether widening is obtained by gingival eviction or retraction.

Gingival eviction is effected either with the aid of an electric bistoury or with the aid of a diamond-charged drill moved by a turbine (rotary curetting).

When an electric bistoury is used, an incision is made, starting from the summit of the gingival scallop and directed towards the bottom of the gingival groove, also called sulcus. The incized tissues are eliminated.

Although leading to a widening of the gingival sulcus with a suitable haemostasis, this method is mutilating and painful and generally requires a local anaesthesia. In addition, it causes a retraction of the gum.

When a diamond-charged drill is used, gingival eviction is effected by dilacerating the marginal gum by the action of the drill, to which is imparted a movement inside the sulcus in order to make a bevel at the level of the limit of the preparation.

This method which is used only in certain specific cases, presents the same drawbacks as the one described previously with reference to the electric bistoury. Bleeding is more prolific and requires a secondary haemostasis.

The processes of gingival retraction are characterized by the positioning in the gingival sulcus of an insert material.

The most current method consists in using a stranded or plaited cotton cord impregnated or not with a solution intended to promote retraction.

This cord is inserted with the aid of a metal double-bend instrument into the sulcus beyond the limit of preparation, before or after the cut of the tooth depending on the methods and type of limit sought.

However, this method suffers from various drawbacks.

Firstly, the positioning of the cord over the whole periphery of the tooth is delicate.

In addition, this process is relatively painful and generally requires a local anaesthesia. Moreover, a frequent lesion is observed of the epithelial attachment as well as haemorrhages or oozing upon withdrawal of the cord for making the impression.

Another method of gingival retraction consists in using, as insert material, a ring made with the aid of a spongy material which may be impregnated with various solutions (haemostatic, astringent, etc. . . ).

The results and drawbacks of this method are identical to those described previously with reference to the use of a cotton cord.

A third method of gingival retraction consists in placing on the prepared tooth a cap made of a spongy material which may be impregnated with various solutions and ensuring retraction by application of an occlusal pressure.

Although rapid and easy to carry out, this method is imprecise and does not ensure a sufficient retraction. It is therefore used at present only to ensure haemostasis after a procedure of gingival eviction.

Finally, it has also been proposed to use, as insert materials, compositions of which certain are used for impression-making, taking the form of an injectable fluid product capable of hardening either by chemical reaction (prior mixture with a hardener) or by physical swelling (absorption of water).

This state of the art is illustrated in particular in documents DE-A-3 737 552, DE-A-3 736 155 and EP-A-0.092 329.

However, such fluid compositions are very difficult to place in the gingival sulcus which is a virtual space whose widening can be obtained only under the effect of a relatively high force.

In addition, it is impossible, with the aid of these "hardening" compositions, to obtain a controlled retraction of the gum and the use of such compositions is relatively slow.

The present invention therefore has for an object to solve the drawbacks set forth hereinabove, by proposing a novel insert material allowing a wide, regular retraction to be obtained over the whole periphery of the tooth, which causes no noteworthy lesion of the marginal gum and which may easily be carried out without bleeding or oozing.

The solution according to the present invention for solving this technical problem, consists in an insert material used for widening the gingival sulcus, substantially without bleeding or oozing, characterized in that it takes the form of a biocompatible paste which is injectable for external use, preferably hydrophilic, and whose rheological properties are such that they oppose the force tending to apply the marginal gum against the tooth without lesion of the adjacent anatomical structures.

According to a particular characteristic, this paste presents a viscosity higher than about 13000 Pascals·second.

Such a material may be easily injected between the tooth and the gum and its consistency makes it possible to obtain a perfectly controlled widening of the gingival sulcus.

The viscosity defined hereinabove is a plastic viscosity measured at 20° C.

According to another characteristic, this paste presents a flow threshold value higher than about 4500 Newtons per m².

According to a presently preferred embodiment, this material comprises clay, in particular a micronized kaolin (China clay), and water.

This material possibly comprises in addition agents modifying the organoleptic and chromatic properties and/or an astringent agent and/or an antiseptic agent.

The use of such a material according to the invention allows the elaboration of an improved method of gingival retraction which does not suffer the various drawbacks of the methods used heretofore. In fact, this method is hardly aggressive as it causes virtually no bleeding or oozing and is consequently painless.

In addition, the pressure exerted on the gingival tissues being solely a function of the viscosity of the insert material, there is no noteworthy lesion of the marginal gum and retraction is thus reversible.

The invention will be more readily understood and other purposes, characteristics and advantages thereof will appear more clearly from the following explanatory description made with reference to the accompanying schematic drawings given solely by way of illustration and in which.

Figure 1:
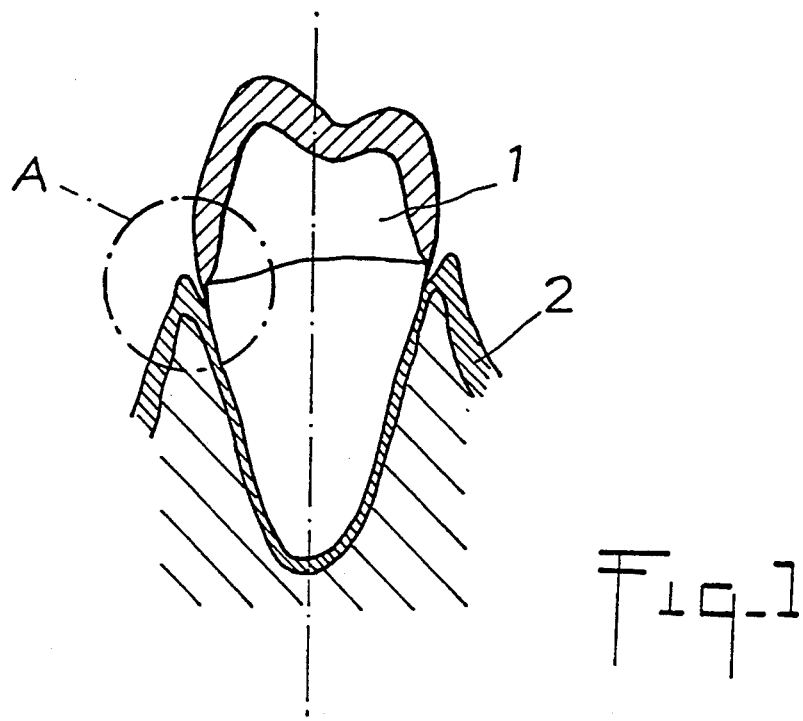
FIG. 1 is a schematic view in transverse section showing a tooth.

FIG. 1 therefore schematically shows a tooth 1 and the gum 2 surrounding its base.

Figure 2:
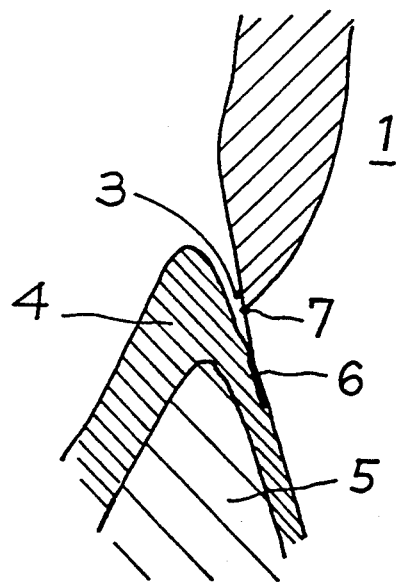
FIG. 2 is a view in transverse section of detail A of FIG. 1.

FIG. 2, which is an enlarged view of detail A of FIG. 1, shows the gingival sulcus 3 included between tooth 1 and the marginal gum 4.

Reference 5 represents the alveolar bone and reference 6 the epithelial attachment.

Reference 7 represents the limit of preparation of the tooth which is located between the epithelial attachment 6 and the upper part of the marginal gum 4.

The hatched part in FIG. 2 represents the sealed portion intended to form prosthesis.

The originality of the present invention consists in using an insert material taking the form of a paste whose rheological properties are such that they oppose the force tending to apply the marginal gum against the tooth without lesion of the adjacent anatomical structures.

This paste must present a perfect biocompatibility and be injectable with a small diameter, for example 0.3 mm to 1.5 mm.

Numerous products presenting these properties may be used, such as for example clays, waxes or other biocompatible materials.

According to a first embodiment of the invention, a material will be used comprising seaweed meal, particularly laminary and in particular laminaria digitata.

The viscosity of this material based on algae may be adjusted, within the preferred ranges mentioned above, with the aid of water.

According to a presently preferred embodiment of the invention, a material will be used, comprising clay, in particular a micronized kaolin, and, there again, the viscosity may easily be adjusted within the preferred ranges with the aid of water.

Furthermore, various additional agents may be used, such as agents modifying the organoleptic and chromatic properties, astringent and/or antiseptic agents.

By way of example, agents modifying the organoleptic properties may be constituted by or contain at least one of the following constituents:

essential oil of lime, orange, mint,
sodium bicarbonate
10 vol. hydrogen peroxide.

By way of example, agents modifying the chromatic properties may be constituted by or contain at least one of the following constituents:

10 vol. hydrogen peroxide,
zinc oxide
white clay
various alimentary colorants.

By way of example, astringent agents may be constituted by or contain at least one of the following constituents:

aluminium chloride,
iron (III) chloride,
iron (III) sulfate,
alums (double aluminium and potassium sulfate).

By way of example, haemostatic agents may be constituted by or contain at least one of the following constituents:

calcium alginate,
oxyquinol
10 vol. hydrogen peroxide.

Finally, by way of antiseptic, digluconate of chlorexidine may be used.

The hydrophilic products generally lead to better results than the hydrophobic products.

A presently preferred composition of insert material according to the invention is the following:

| | |
|---|---|
| white clay (micronized kaolin) | 65 to 70% by weight |
| aluminium chloride | 3.6 to 6.8% by weight |
| H$_2$O | 24 to 27% by weight |
| essential oil | 0.33% by weight |
| colorant (E 102 + E 131) | 1% by weight |

Several compositions of material according to the present invention are given in Examples 1 to 7.

EXAMPLE 1

| | |
|---|---|
| white clay | 66.75% |
| aluminium chloride | 6.54% |
| H$_2$O | 25.36% |
| essential oil of lemon | 0.33% |
| colorant (E 102 + E 131) | 1.02% |

EXAMPLE 2

| | |
|---|---|
| white clay | 65.60% |
| aluminium chloride | 6.83% |
| H$_2$O | 26.24% |
| essential oil of lemon | 0.33% |
| colorant (E 102 + E 131) | 1.00% |

EXAMPLE 3

| | |
|---|---|
| white clay | 69.83% |
| aluminium chloride | 3.64% |
| H$_2$O | 25.14% |
| essential oil of lemon | 0.35 |
| colorant (E 102 + E 131) | 1.04% |

EXAMPLE 4

| | |
|---|---|
| seaweed meal | 46% |
| water | 54% |

EXAMPLE 5

| | |
|---|---|
| micronized seaweed meal laminaria digitata | 46.1% |
| distilled water | 53.85% |
| digluconate of chlorexidine | 0.05% |

EXAMPLE 6

| | |
|---|---|
| micronized seaweed meal laminaria digitata | 45.63% |
| 10 vol. hydrogen peroxide | 45.63% |
| essential oil of orange | 1.14% |
| zinc oxide | 7.55% |
| digluconate of chlorexidine | 0.05% |

EXAMPLE 7

| | |
|---|---|
| micronized seaweed meal laminaria digitata | 34.08% |
| white clay | 19.47% |
| 10 vol. hydrogen peroxide | 43.82% |
| sodium bicarbonate | 2.43% |
| essential oil of orange | 0.20% |

The materials thus prepared, based on algae, behave like Bingham plastics. They present a plastic viscosity at 20° C. of between about 13000 and about 30000 Pascals·second, a flow threshold of about 5000 Newtons/m² (measurements made in creep with the aid of a flow meter with imposed strain provided with a plane-cone device at 20° C. (cone with a diameter of 1.5 cm, angle of 4°).

The materials based on clay are characterized by the following values:
flow threshold greater than about 4500 Newtons/m²;
dynamic viscosity greater than about 27000 Pascals. second (under a strain of 9000 Newtons/m² and a speed of 0.3 s.$^{-1}$).

A material according to the present invention may be inserted in the gingival sulcus by injection by means of a cylindrical or conical needle whose end presents a slot of diameter included between about 0.3 and 1.5 mm.

This needle advantageously presents a bend of about 30°.

A sterilizable or one-use needle capable of being changed after each operation will be used.

The diameter of the needle will be selected depending on the type of preparation and limit as well as on the size of the gingival sulcus. In this way, a needle with a diameter of about 1 to 1.5 mm will be used for a wide groove, and of 0.5 mm for a limit in bevel.

The depth of the sulcus, the thickness and tonicity of the marginal gum are variable on the periphery of the same tooth, with the result that it is desirable to be able to check the magnitude of the retraction sought at each point.

The injection of a pasty product makes it possible, by depositing more or less product, to obtain a wide, regular retraction over the whole periphery of the tooth.

The injection of the pasty product in the gingival sulcus is effected by abutting on the tooth and exerting no pressure with the needle on the tissues.

As will be readily understood, the pressure exerted on the gingival tissues is solely a function of the viscosity of the product.

In this way, a wide, regular retraction is obtained over the whole periphery of the tooth.

Figure 3:
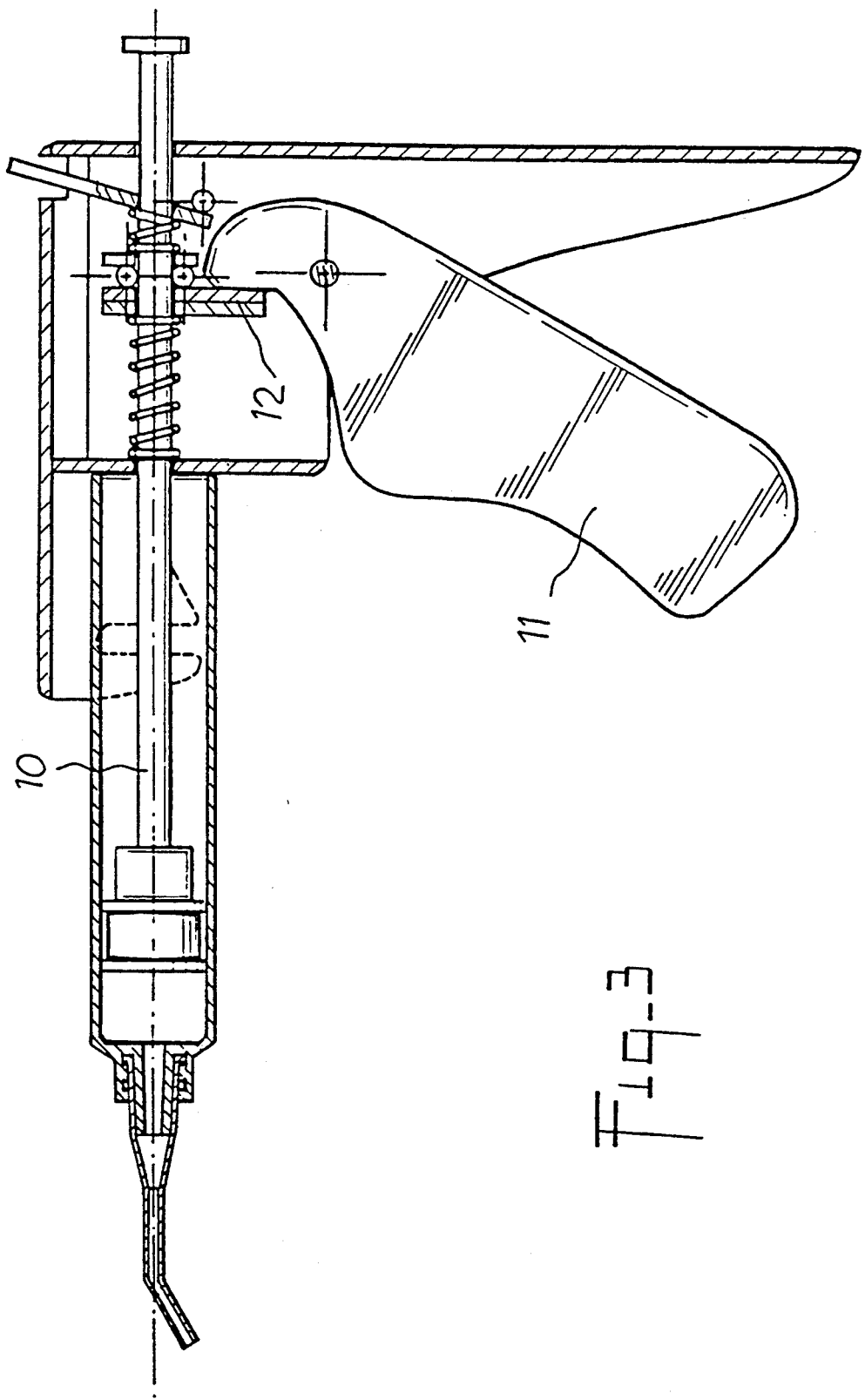
FIG. 3 is a view in transverse section of a syringe allowing the insertion by injection of a material according to the invention.

FIG. 3 shows a presently preferred embodiment of an injection device for placing the insert material according to the invention in position. In fact, the product used having a relatively high viscosity, the pressure developed in a conventional syringe is not sufficient.

A syringe such as the one shown in FIG. 3 may therefore be used, of which the active part 10 is driven by a plate 12, itself moved by the handle 11, transmitting, on multiplying it by lever effect, the force developed between the fingers and the palm of the hand.

The material according to the invention may be eliminated under the action of an air and water spray without intervention of instrument prior to the taking of an impression. Any risk of injury to the tissues is thus avoided.

Finally, it should be noted that the material according to the invention may also be used after a procedure of gingival eviction by electrical bistoury or rotary curettage to ensure haemostasis and to maintain the widening of the gingival sulcus.

As will be readily understood, the use of the material according to the present invention allows an improved method of gingival retraction to be carried out, which, for the first time, groups together all the following advantages:
easy accessibility of the limit of preparation;
absence of lesion of the tissues;
reversible retraction;
rapid, easy and painless execution.

I claim:

1. A method for widening the gingival sulcus, without bleeding or oozing, comprising inserting within the gingival sulcus a material in the form of a biocompatible paste which is injectable for external use, preferably hydrophilic, and having a plastic viscosity measured at 20° C. between about 13,000 and 30,000 Pascals second, wherein said material consisting of a material selected from the group of white clay, seaweed meal and mixtures thereof.

2. A method according to claim 1, wherein the insertion is made by injection.

3. A method according to one of claims 1 and 2, wherein said paste material has a flow threshold greater than about 4500 Newtons/m².

4. A method according to claim 1, wherein said seaweed meal is a laminary algae.

5. A method according to claim 4, wherein the laminary algae is laminaria digitata.

6. A method according to claim 1, wherein said material includes an agent modifying the organoleptic properties of said material.

7. A method according to claim 5, wherein the organoleptic property-modifying agent is selected from the group consisting of essential oils, sodium bicarbonate, 10 vol.% hydrogen peroxide, and combinations thereof.

8. A method according to claim 6, wherein the essential oils are selected from the group consisting of essential oils of lime, orange and mint.

9. A method according to claim 6, wherein said material further comprises an agent for modifying the chromatic properties of the material.

10. A method according to claim 8, wherein the chromatic properties-modifying agent is selected from the group consisting of zinc oxide, white clay, alimentary colorants and 10 vol.% hydrogen peroxide.

11. A method according to claim 9, wherein said material further comprises an agent selected from the group of astringent and antiseptic agents and combinations thereof.

12. A method according to claim 1, wherein said material includes an agent modifying the organoleptic properties of said material.

13. A method according to claim 12, wherein the organoleptic property-modifying agent is selected from the group consisting of essential oils, sodium bicarbonate, 10 vol.% hydrogen peroxide, and combinations thereof.

14. A method according to claim 13, wherein the essential oils are selected from the group consisting of essential oils of lime, orange and mint.

15. A method according to claim 13, wherein said material further comprises an agent for modifying the chromatic properties of the material.

16. A method according to claim 15, wherein the chromatic properties-modifying agent is selected from the group consisting of zinc oxide, white clay, alimentary colorants and 10 vol.% hydrogen peroxide.

17. A method according to claim 15, wherein the material further comprises an agent selected from the group of astringent and antiseptic agents and combinations thereof.

18. A method according to claim 1, wherein said material comprises, by weight percent:

| | | |
|---|---|---|
| seaweed meal | 46% | |
| water | 54%. | |

19. A method according to claim 18, wherein said material comprises, by weight percent, about:

| | |
|---|---|
| micronized seaweed meal consisting of laminaria digitata | 45.63% |
| 10 vol. % hydrogen peroxide | 45.63% |
| essential oil of orange | 1.14% |
| zinc oxide | 7.55% |
| digluconate of chlorexidine | 0.05%. |

20. A method according to claim 18, wherein said material comprises, by weight percent, about:

| | |
|---|---|
| micronized seaweed meal consisting of laminaria digitata | 34.08% |
| white clay | 19.47% |
| 10 vol. % hydrogen peroxide | 43.82% |
| sodium bicarbonate | 2.43% |
| essential oil of orange | 0.20%. |

21. A method according to claim 10, wherein said material comprises, by weight percent, about:

| | |
|---|---|
| white clay (micronized kaolin) | 65 to 70% |
| aluminum chloride | 3.6 to 6.8% |
| water | 24 to 27% |
| essential oil | 0.33%. |
| colorant | 1%. |

* * * * *